US009039608B2

(12) United States Patent
Donhowe et al.

(10) Patent No.: US 9,039,608 B2
(45) Date of Patent: May 26, 2015

(54) METHOD AND SYSTEM FOR AUTOMATICALLY MAINTAINING AN OPERATOR SELECTED ROLL ORIENTATION AT A DISTAL TIP OF A ROBOTIC ENDOSCOPE

(71) Applicant: Intuitive Surgical Operations, Inc., Sunnyvale, CA (US)

(72) Inventors: Caitlin Q. Donhowe, Sunnyvale, CA (US); Giuseppe Maria Prisco, Mountain View, CA (US)

(73) Assignee: INTUITUVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 14/162,449

(22) Filed: Jan. 23, 2014

(65) Prior Publication Data

US 2014/0200407 A1    Jul. 17, 2014

Related U.S. Application Data

(62) Division of application No. 13/013,918, filed on Jan. 26, 2011, now Pat. No. 8,668,638.

(60) Provisional application No. 61/303,365, filed on Feb. 11, 2010.

(51) Int. Cl.
*A61B 1/00* (2006.01)
*A61B 1/005* (2006.01)
(Continued)

(52) U.S. Cl.
CPC ........... *A61B 1/0055* (2013.01); *A61B 1/00147* (2013.01); *A61B 1/0051* (2013.01); *A61B 2019/5261* (2013.01); *A61B 5/065* (2013.01)

(58) Field of Classification Search
CPC ............... A61B 2019/2211; A61B 2017/2929; A61B 2017/293; A61B 19/2203; Y10S 901/02; Y10S 901/14
See application file for complete search history.

(56) References Cited

U.S. PATENT DOCUMENTS 3,985,021 A * 10/1976 Achener et al. .............. 73/61.56
5,103,404 A    4/1992 McIntosh
(Continued)

FOREIGN PATENT DOCUMENTS

EP    1844696 A1    10/2007
EP    2313018 A1    4/2011
(Continued)

OTHER PUBLICATIONS

Bailly, Yan et al., "Modeling and Control of a Hybrid Continuum Active Catheter for Aortic Aneurysm Treatment," Proceedings of the 2005 IEEE International Conference on Robotics and Automation Barcelona, Spain, Apr. 2005, pp. 924-929,IEEE.
(Continued)

*Primary Examiner* — Anhtuan T Nguyen
*Assistant Examiner* — Jae Woo

(57) ABSTRACT

In a robotic endoscope system, the orientation of a captured camera view at a distal tip of a robotic endoscope and displayed on a screen viewable by an operator of the endoscope is automatically maintained at a roll orientation associated with a setpoint so as not to disorient the operator as the endoscope is moved, flexed and its tip turned in different orientations. A processor generates a current commanded state of the tip from operator input and modifies it to maintain the setpoint roll orientation. To generate the modified current commanded state, the current commanded roll position and velocity are constrained to be a modified current commanded roll position and velocity that have been modified according to a roll angular adjustment indicated by a prior process period commanded state of the tip and the setpoint. The processor then commands the robotic endoscope to be driven to the modified commanded state.

14 Claims, 7 Drawing Sheets

(51) Int. Cl.
*A61B 5/06* (2006.01)
*A61B 19/00* (2006.01)

(56) References Cited

U.S. PATENT DOCUMENTS

| | | | |
|---|---|---|---|
| 5,368,015 | A | 11/1994 | Wilk |
| 5,522,788 | A | 6/1996 | Kuzmak |
| 5,638,819 | A | 6/1997 | Manwaring et al. |
| 5,899,851 | A * | 5/1999 | Koninckx ............... 600/117 |
| 6,424,885 | B1 * | 7/2002 | Niemeyer et al. ............ 700/245 |
| 6,425,865 | B1 | 7/2002 | Salcudean et al. |
| 6,459,926 | B1 | 10/2002 | Nowlin et al. |
| 6,471,637 | B1 | 10/2002 | Green et al. |
| 6,665,554 | B1 | 12/2003 | Charles et al. |
| 6,666,854 | B1 | 12/2003 | Lange |
| 6,786,896 | B1 | 9/2004 | Madhani et al. |
| 6,837,883 | B2 | 1/2005 | Moll et al. |
| 7,037,258 | B2 * | 5/2006 | Chatenever et al. .......... 600/109 |
| 7,211,042 | B2 * | 5/2007 | Chatenever et al. .......... 600/117 |
| 7,401,794 | B2 | 7/2008 | Laurent et al. |
| 7,453,227 | B2 | 11/2008 | Prisco et al. |
| 7,833,152 | B2 * | 11/2010 | Chatenever et al. .......... 600/117 |
| 7,865,266 | B2 | 1/2011 | Moll et al. |
| 8,668,638 | B2 | 3/2014 | Donhowe et al. |
| 2002/0128552 | A1 | 9/2002 | Nowlin et al. |
| 2006/0241414 | A1 | 10/2006 | Nowlin et al. |
| 2006/0258938 | A1 * | 11/2006 | Hoffman et al. .............. 600/424 |
| 2007/0173694 | A1 * | 7/2007 | Tsuji et al. .................. 600/146 |
| 2008/0051239 | A1 | 2/2008 | Jinno et al. |
| 2008/0188869 | A1 | 8/2008 | Weitzner et al. |
| 2008/0188871 | A1 | 8/2008 | Smith et al. |
| 2008/0243064 | A1 | 10/2008 | Stahler et al. |
| 2008/0249536 | A1 | 10/2008 | Stahler et al. |
| 2008/0262513 | A1 | 10/2008 | Stahler et al. |
| 2009/0024141 | A1 | 1/2009 | Stahler et al. |
| 2009/0123111 | A1 | 5/2009 | Udd |
| 2009/0137952 | A1 | 5/2009 | Ramamurthy et al. |
| 2009/0138025 | A1 | 5/2009 | Stahler et al. |
| 2010/0076263 | A1 * | 3/2010 | Tanaka et al. ................ 600/109 |
| 2010/0228265 | A1 | 9/2010 | Prisco |
| 2010/0332031 | A1 | 12/2010 | Itkowitz et al. |
| 2010/0332033 | A1 * | 12/2010 | Diolaiti et al. ............... 700/259 |
| 2011/0196199 | A1 | 8/2011 | Donhowe et al. |

FOREIGN PATENT DOCUMENTS

| | | |
|---|---|---|
| WO | WO-9729701 A1 | 8/1997 |
| WO | WO-9950721 A1 | 10/1999 |
| WO | WO-2008070556 A1 | 6/2008 |
| WO | WO-2008133956 A2 | 11/2008 |
| WO | WO-2009023801 A1 | 2/2009 |
| WO | WO-2009097461 A1 | 8/2009 |

OTHER PUBLICATIONS

Computer Motion, Inc., "An 8 Degree-of-Freedom Macro-Micro Robot for Precise Force," 1994, 72 Pages Total.

Guittet, Jacques, "The Spartacus Telethesis: Manipulator Control Studies," 1979, pp. 69-105.

Hayashi, Koichiro et al., "Tele-existence Vision System with Image Stabilization for Rescue Robots," Journal of Robotics and Mechatronics, 2005, pp. 181-188, vol. 17—No. 2.

Jayender J. et al., "Master-Slave Control of an Active Catheter Instrumented with Shape Memory Alloy Actuators," Proceedings of the 2007 IEEE/RSJ International Conference on Intelligent Robots and Systems, 2007, pp. 759-764, IEEE.

Park, Jaeheung et al., "A Haptic Teleoperation Approach Based on Contact Force Control," The International Journal of Robotics Research, 2006, pp. 575-591, vol. 25, Issue 5-6, SAGE Publications.

PCT/US11/22493 International Search Report and Written Opinion of the International Searching Authority, mailed May 13, 2011, 9 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wendlandt, Jeff M. et al., "Design and Control of a Simplified Stewart Platform for Endoscopy," Proceedings of the 33rd conference on Decision and control, 1994, pp. 357-362, IEEE.

\* cited by examiner

METHOD AND SYSTEM FOR AUTOMATICALLY MAINTAINING AN OPERATOR SELECTED ROLL ORIENTATION AT A DISTAL TIP OF A ROBOTIC ENDOSCOPE

CROSS REFERENCE TO RELATED APPLICATIONS

This application is a divisional of application Ser. No. 13/013,918, filed Jan. 26, 2011, which is incorporated herein by reference.

The present application claims the benefit of U.S. Provisional Application No. 61/303,365, entitled "METHOD AND SYSTEM FOR AUTOMATICALLY MAINTAINING AN OPERATOR SELECTED ROLL ORIENTATION AT A DISTAL TIP OF A ROBOTIC ENDOSCOPE" filed on Feb. 11, 2010.

FIELD OF THE INVENTION

The present invention generally relates to robotic endoscopes and in particular, to a method and system for automatically maintaining an operator selected roll orientation at a distal tip of a robotic endoscope while controlling operator commanded movement of the robotic endoscope tip.

BACKGROUND OF THE INVENTION

An endoscope is a medical device that allows physicians to capture images of and diagnose problems with internal body organs by inserting the device either through a natural orifice or a surgeon created opening and guiding it to a target site within a patient. In some cases, it may also be used to perform medical procedures on the internal body organs. It may be steerable so that its distal tip is controllably oriented and positioned for navigation purposes. An image capturing device such as a stereoscopic or monoscopic camera may be provided at its distal tip so that images captured by the camera from that perspective may be viewed on a display screen by the surgeon. To perform various medical procedures at the target site, surgical tools, such as those used for cutting, grasping, cauterizing, etc., may extend out of the endoscope's distal tip.

The endoscope may be rigid such as those used in laparoscopy or it may be flexible so that it is capable of following the curvatures of body lumens. It may also be rigidizable and/or robotic. A rigidizable endoscope is an endoscope that has at least one section of its flexible body that can be made substantially rigid by a mechanical locking mechanism. A robotic endoscope is a flexible endoscope that has at least one section that bends under a computer controlled servo mechanism.

Natural Orifice Transluminal Endoscopic Surgery ("NOTES") may employ a steerable endoscope to perform surgical procedures on patients. As an example, a flexible endoscope may be guided through one of the body's orifices and enter the abdomen from the inside of the patient, rather than through a minimally invasive incision from the outside. For example, in "transgastric" surgery, instruments are passed through the mouth and into the stomach. A gastrotomy is then performed so that the instruments may enter the abdomen and be used by the surgeon to perform a medical procedure within the abdominal cavity. Once the procedure is completed, the instruments are withdrawn along with any tissue removed during the procedure, and the entry point is closed back up. Because no external incisions are made in the patient to accommodate entry of the endoscope, NOTES may be even less painful than surgery using minimally invasive incisions. Also, since it uses a natural body orifice instead of external incisions to enter the body, it may result in reduced needs for general anesthetics and faster recovery times.

During the operation of an endoscope, the endoscope tip may be turned multiple times and in different directions while moving towards, or while performing a medical procedure at, a target site. As a consequence, the orientation of images captured at the distal tip of the endoscope may change and it operator may become disoriented when viewing the captured images. If the operator accidentally moves the endoscope tip in the wrong direction as a result of such disorientation, the tip may inadvertently perforate or otherwise damage tissue causing harm to the patient. Even if such harm is avoided by carefully moving the endoscope tip, additional time is required to repeatedly ascertain the true orientation of the endoscope tip relative to the target site in the patient. Thus, the time required to perform the procedure is lengthened which adds to the cost of the surgery and increases health safety concerns.

U.S. Pat. No. 7,134,992 to Schara et al. (2006), which is incorporated herein by reference, discloses a method for presenting an endoscope image in a gravity referenced, upright orientation by sensing a rotation of the endoscope and rotating the endoscopic image accordingly to compensate for the sensed rotation before displaying the rotated image on a video display device.

One problem with such an image rotation technique is that when tools extend out of the distal end of the endoscope, they may not be oriented correctly from the operator's viewpoint of a captured image for the task at hand. Also, although it may be convenient to use gravity as a reference for orienting the image, it is desirable to eliminate the cost and complexity of additional hardware dedicated to sensing the direction of gravity. Further, it may be useful at times to provide the operator with a means to select a different orientational reference.

OBJECTS AND SUMMARY OF THE INVENTION

Accordingly, one object of one or more aspects of the present invention is a method, and a system for performing the method, of automatically maintaining a desired roll orientation at a distal tip of a robotic endoscope while moving the robotic endoscope tip towards or at a target site within a patient.

Another object of one or more aspects of the present invention is a method, and a system for performing the method, of automatically maintaining a desired roll orientation at a distal tip of a robotic endoscope without need for a roll angle sensor at the distal tip.

Still another object of one or more aspects of the present invention is a method, and a system for performing the method, of providing a means for an operator to select a desired roll orientation that is to be automatically maintained at a distal tip of a robotic endoscope.

These and additional objects are accomplished by the various aspects of the present invention, wherein briefly stated, one aspect is a computer implemented method for controlling operator commanded movement of a distal tip of a robotic endoscope while maintaining a roll orientation at the tip, the method comprising: receiving a control input from an operator manipulatable input control device; determining a current commanded state of the tip of the robotic endoscope from the control input, wherein the current commanded state includes a current commanded roll position and velocity; modifying the current commanded state by constraining the current commanded roll position and velocity to be a modified current commanded roll position and velocity according to a roll angular adjustment indicated by a prior process period commanded state of the tip and a setpoint indicative of the roll orientation to be maintained at the tip; and commanding the tip of the robotic endoscope to be driven to the modified current commanded state.

Another aspect is a medical robotic system comprising: a robotic endoscope having an elongate body including one or more bendable segments and a distal tip; a manipulator having one or more drivable joints for manipulating the robotic endoscope in corresponding degrees of freedom movement; an operator manipulatable input control device; and a processor configured to receive a control input from the operator manipulatable input control device, determine a current commanded state of the tip of the robotic endoscope from the control input wherein the current commanded state includes a current commanded roll position and velocity, modify the current commanded state by constraining the current commanded roll position and velocity to be a modified current commanded roll position and velocity according to a roll angular adjustment indicated by a prior process period commanded state of the tip and a setpoint indicative of the roll orientation to be maintained at the tip, and commanding the tip of the robotic endoscope to be driven to the modified current commanded state.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
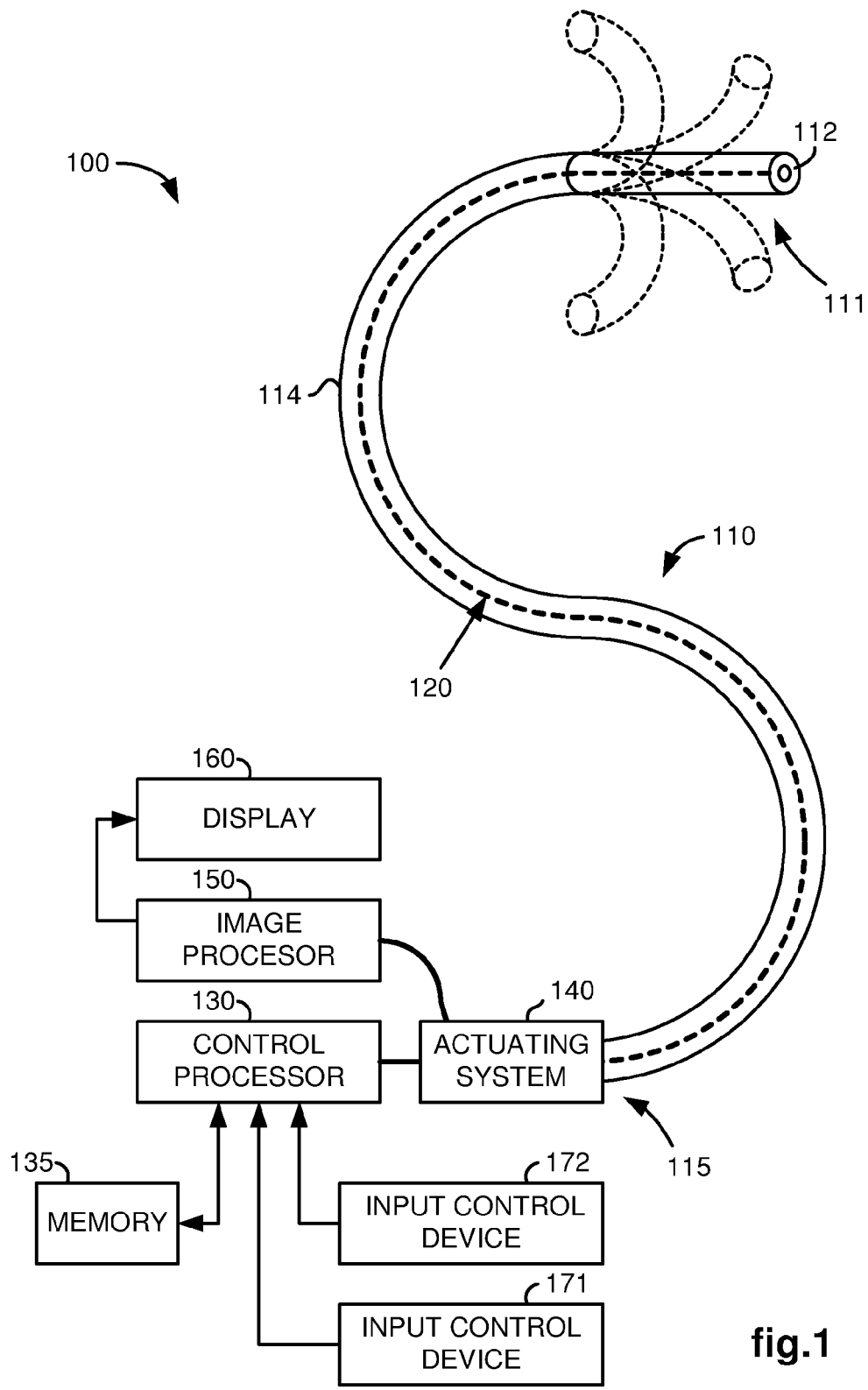
FIG. 1 illustrates a medical robotic system utilizing aspects of the present invention.

FIG. 1 illustrates, as an example, a medical robotic system 100 including a robotic endoscope 110, a plurality of fiber optic cables 120 inserted in the endoscope 110, a control processor 130 with memory 135, an actuating system 140, an image processor 150, a display screen 160, and input control devices 171, 172. The control processor 130 and image processor 150 (as well as any other processors or controllers described herein) may each be implemented as hardware, firmware, software or a combination thereof, which interact with or are implemented in one or more computers. The display screen 160 preferably comprises left and right eye screens incorporated in a computer monitor so as to be capable of displaying three-dimensional images to an operator of the system 100. However, for cost considerations, it may be a standard computer monitor capable of only displaying two-dimensional images. Although only one display screen is shown, additional display screens may be provided so that, for example, an assistant may view a display screen that has been positioned near the assistant while the surgeon is viewing the display screen 160. The input control device 171 is preferably a six-dimensional (6-D) joystick (either rate or position type) capable of commanding at least six degrees-of-freedom (DOF) movement (e.g., three translational and three orientational). The input control device 172, on the other hand, may be a conventional computer input device such as a computer mouse or keyboard.

The robotic endoscope 110 has a flexible elongate body 114 with preferably at least two controllably bendable segments. It has at least one controllably bendable segment that results in a steerable tip 112 at its distal end 111. It also has an actuating system 140 coupled to its proximal end 115 for actuating movement of the endoscope 110 and its controllably bendable segments. Control cables or other conventional control means (not shown) extend from the actuating system 140 to the at least one controllably bendable segment of the steerable tip 112 so that the tip 112 may be controllably bent or turned, as shown for example by dotted line versions of the bent tip 112. Other cables or other conventional control means (not shown) may also extend in this example to other controllably bendable segments so that they may be controllably bent. Passive bendable segments may also be included in the robotic endoscope as well as bendable segments that are constrained in some fashion to move with other bendable segments.

Figure 2:
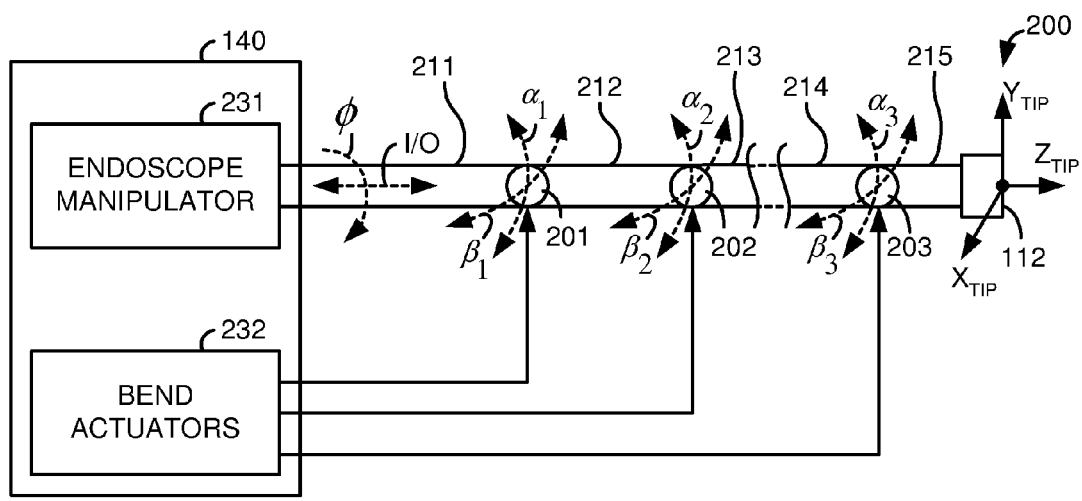
FIG. 2 illustrates a schematic diagram of a robotic endoscope of the medical robotic system utilizing aspects of the present invention.

Referring to FIG. 2, the actuating system 140 includes an endoscope manipulator 231 and one or more bend actuators 232. The endoscope manipulator 231 serves to actuate the robotic endoscope 110 in two degrees of freedom. One degree of freedom is an insertion/retraction movement (as illustrated by the dotted line, two-headed arrow labeled "I/O") implemented with a prismatic joint that moves the proximal end 115 of the robotic endoscope 110 forward and backward. The other degree of freedom is a proximal roll rotation (as illustrated by the dotted line, two-headed arrow labeled "φ") implemented with a rotary joint that rotates the robotic endoscope 110 about its insertion/retraction direction. The bend actuators 232 actuate bending segments 201-203 of the robotic endoscope 110 so they are each bendable in respective pitch rotations (as illustrated by the dotted line, two-headed arcs $\alpha_1$-$\alpha_3$) and yaw rotations (as illustrated by the dotted line, two-headed arcs ($\beta_1$-$\beta_3$). In addition to the bendable segments, a first link 211 of the robotic endoscope 110 is coupled at its proximal end to the endoscope manipulator 231 and at its distal end to rest of the body 114 so that as the endoscope manipulator 231 causes the link 211 to move in either the I/O direction or roll rotation ($\phi$), then the rest of the body 114 (and in particular, all of the bendable segments 201-203 and coupling links 212-215 that couple with the bendable segments 201-203) move in unison with the first link 211.

One or more of the fiber optic cables 120 (shown in FIG. 1) are preferably configured with bend or shape sensors such as Fiber Bragg Gratings (or other strain sensors such as those employing Rayleigh scattering) so that light passing through the fiber optic cable is processed by the control processor 130 (or a separate position processor) to determine a current position and shape of the endoscope 110 including the orientation of its distal tip 112. In addition to the fiber optic cables 120 extending through the endoscope 110, one or more additional fiber optic cables (not shown) configured with strain sensors may be attached to the endoscope 110 so as to provide position information of the endoscope 110 at the attachment point. Additional details on the determination of the endoscope's position and bending using Fiber Bragg Gratings may be found, for examples, in U.S. 2007/0156019 A1 entitled "Robotic Surgery System Including Position Sensors Using Fiber Bragg Gratings"; U.S. 2008/0212082 A1 entitled "Fiber Optic Position and/or Shape Sensing Based on Rayleigh Scatter"; U.S. 2008/0218770 A1 entitled "Robotic Surgical Instrument and Methods using Bragg Fiber Sensors"; and U.S. application Ser. No. 12/164,829 entitled "Fiber Optic Shape Sensor; each of which is incorporated herein by reference. Additional details for a conventional steerable endoscope may be found for example in U.S. Pat. No. 6,869,396 B2 entitled "Steerable Endoscope and Improved Method of Insertion", which is incorporated herein by reference. Although fiber optic sensors are the preferred means for bend or shape sensing, other sensors may also be used in practicing the present invention, such as electro-magnetic sensors, potentiometers, etc.

A stereoscopic or monoscopic camera is provided at the distal tip 112 of the endoscope 110 for capturing images that are transmitted to and processed by the image processor 150 and displayed on the display screen 160 in a conventional manner for endoscopes. One of the fiber optic cables 120 may be coupled at its proximal end to a light source (not shown) for illumination purposes at the distal tip 112. A distal tip reference frame 200 is defined at the distal tip 112 by a depth axis $Z_{TIP}$, a horizontal axis $X_{TIP}$ and a vertical axis $Y_{TIP}$ of a view of the camera as it looks away from the distal tip 112.

Figure 3:
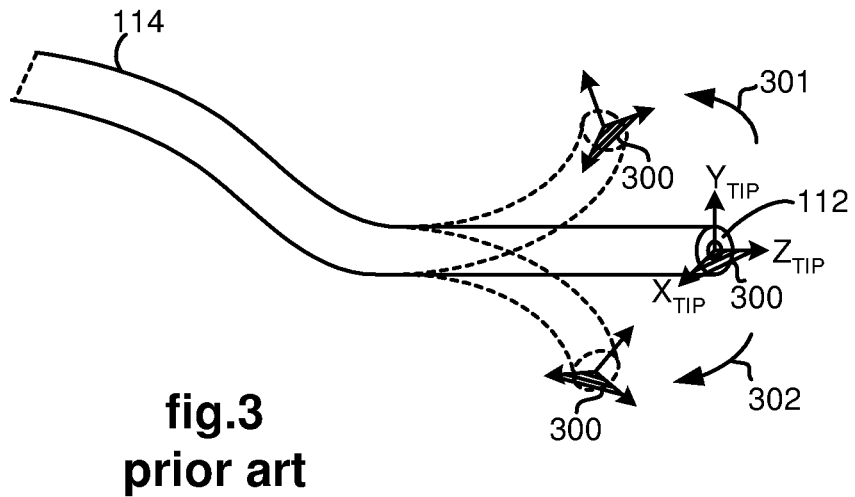
FIG. 3 illustrates a tip of a robotic endoscope being oriented in different directions without roll orientation compensation.
Figure 4:
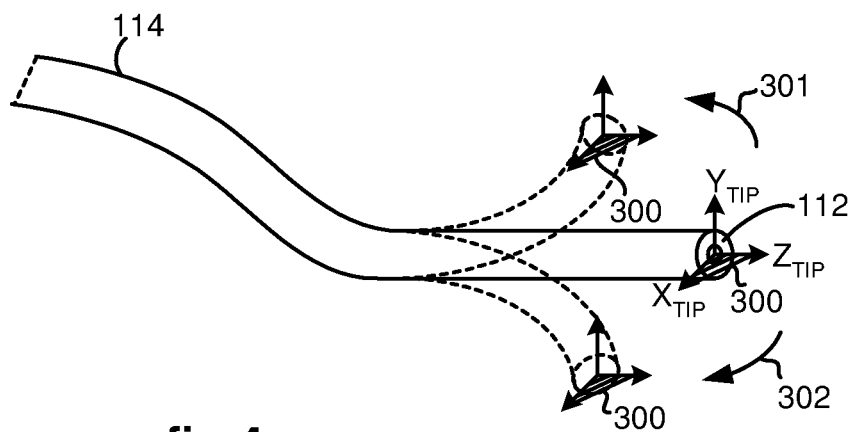
FIG. 4 illustrates a tip of a robotic endoscope being oriented in different directions with roll orientation compensation according to aspects of the present invention.

As simplistically shown in FIG. 3, when the distal tip 112 is bent in one direction 301 or another direction 302, its horizontal orientation 300 (as defined by the $X_{TIP}$-$Z_{TIP}$ plane) may change with respect to its surroundings. As previously explained, such changes in horizontal orientation relative to the surroundings may disorient the operator as the operator views the area from images that are captured by the distal tip camera and displayed on the display screen 160. To prevent such disorientation, ideally, as shown in FIG. 4, when the distal tip 112 is bent in any direction, its horizontal orientation 300 remains the same with respect to its surroundings. For example, it may be desired that the horizontal orientation 300 is always perpendicular to the force of gravity.

Figure 5:
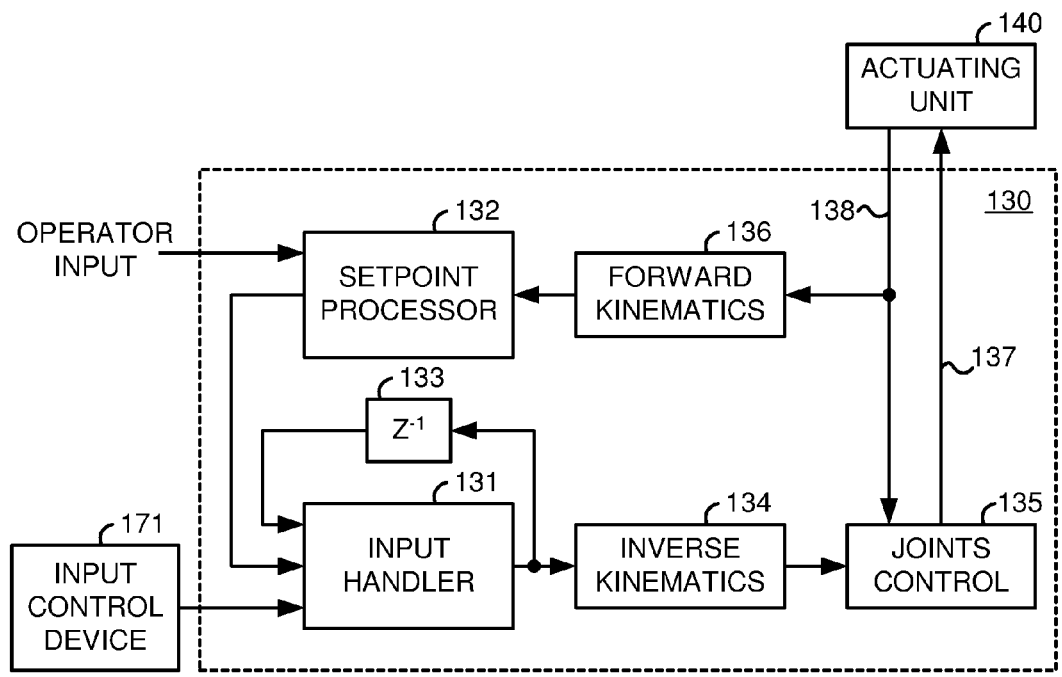
FIG. 5 illustrates a block diagram of components of a control processor for operator selection of a setpoint and control of a tip of the robotic endoscope, as included in the medical robotic system utilizing aspects of the present invention.

FIG. 5 illustrates, as an example, a block diagram of components of the control processor 130 that allow an operator to select or change a setpoint, which indicates a desired roll orientation of a camera view captured at the distal tip 112 of the robotic endoscope 110, and to command movement of the distal tip 112 while the system automatically maintains the desired roll orientation at the distal tip 112. The operator interacts with a setpoint processor 132 using an appropriate input device such as the input control device 172 to select or change the setpoint and commands movement of the distal tip 112 of the robotic endoscope 110 using the input control device 171.

An initial or default setpoint may be established with or without operator intervention using gravity to generate a reference. In this case, a reference vector $Y_{SP}$ indicating the setpoint may be defined so that it points in an opposite direction from the gravity vector. The setpoint may subsequently be changed (or initially established if a default setpoint has not been defined) by the operator interacting with the setpoint processor 132. For example, the operator may select the setpoint so that it corresponds to a current roll orientation of the tip 112 by depressing a select button on one of the input control devices 171, 172, or using a voice command recognized for such purpose by a voice recognition system (not shown), or using any other well known interactive means. In this case, the setpoint processor 132 defines the reference vector $Y_{SP}$ indicating the setpoint so that it points in the same direction as the $Y_{TIP}$ axis of the tip's camera view at the time of such operator selection input. The tip reference frame ($X_{TIP}$, $Y_{TIP}$, $Z_{TIP}$) is determined in a conventional manner from a current tip position and orientation generated by forward kinematics processor 136 from sensed joint positions 138 of the actuating unit 140.

Figure 6:
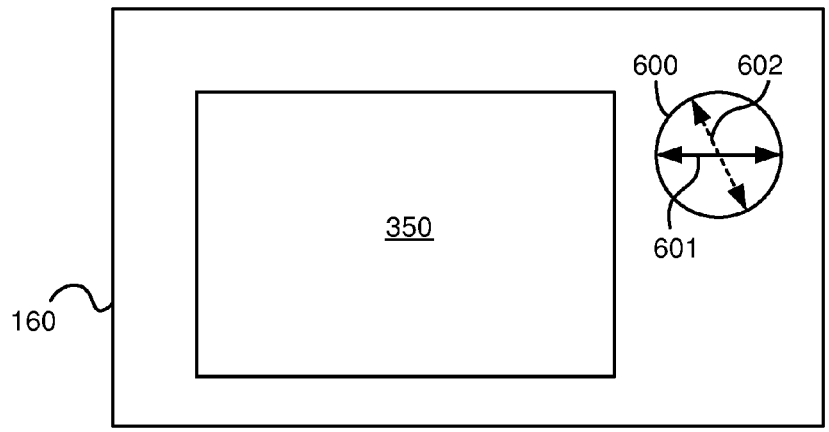
FIG. 6 illustrates a display screen displaying an image captured by a camera at a distal tip of a robotic endoscope and a graphical representation of current roll angle and roll setpoint indicators as viewed on a display of the medical robotic system utilizing aspects of the present invention.

As another example, the operator may establish the setpoint by interacting with a Graphical User Interface (GUI). As illustrated in FIG. 6, the setpoint processor 132 may be implemented to include the GUI which includes the display screen 160 upon which a graphics image 600 is displayed adjacent an image 350 captured by the distal tip camera. The graphics image 600 includes a current roll angle indicator 601 and a graphically rotatable roll setpoint indicator 602. The GUI allows an input control device such as the input control device 172 to interact with the rotatable roll setpoint indicator 602 of the graphics image 600. For example, in response to movement of the input control device 172 by its operator, the roll setpoint indicator 602 may be rotated to a different angle, as shown in FIG. 6, from the current roll angle indicator 601. Meanwhile, as the operator causes the roll setpoint indicator 602 to rotate, the input handler 131 causes the distal tip roll angle ($\phi_{tip}$) and the current roll angle indicator 601 to track the movement so that when the distal tip roll angle matches the angle indicated by the rotatable roll setpoint indicator 602, the selectable roll setpoint indicator 602 disappears on the display screen 160 and the current roll angle indicator 601 remains.

Referring back to FIG. 5, the operator commands movement of the distal tip 112 of the robotic endoscope 110 by moving the input control device 171. If the input control device 171 is a position type device, its movement defines 6 DOF of translational and orientational positions. In this case, 6 DOF of translational and orientational velocities may be calculated in a conventional manner by dividing corresponding changes in position between successive process periods by the duration of a process period. On the other hand, if the input control device 171 is a rate type device, its movement defines 6 DOF of translational and orientational velocities. In this latter case, 6 DOF of translational and orientational positions may each be calculated in a conventional manner by adding the product of a corresponding velocity and the duration of the process period to a position value calculated (or initially set) for the immediately prior process cycle. In either case, the additional velocity or position calculations are performed by an input processor that is considered, for the purposes of simplifying the description, part of the input control device 171.

The input handler processor 131 processes the output of the input control device 171 to generate a current commanded state of the distal tip 112 relative to a fixed Cartesian X, Y, Z reference frame (e.g., fixed frame 800 of FIG. 8) and modifies the current commanded state using information of the setpoint provided by the setpoint processor 132 to generate a modified current commanded state of the distal tip 112. A detailed description of the processing performed by the input handler processor 131 is described herein in reference to FIGS. 7-10. The modified current commanded state takes into account both the operator commanded movement of the distal tip 112 and the requirement to maintain the roll orientation at the distal tip 112 (i.e., maintain the angle of the horizon defined by the $X_{TIP}$-$Z_{TIP}$ plane of the distal tip camera view relative to a reference vector $Y_{SP}$ associated with the setpoint).

An inverse kinematics processor 134 receives the commanded state of the distal tip 112 from the input handler processor 131 and transforms it to corresponding joint commands for driving the endoscope manipulator 231 and bend actuators 232. The transformation is performed by applying the commanded state in a conventional manner to inverse kinematics of the combined serial kinematic chain composed of the endoscope manipulator 231 and the robotic endoscope 110. A joint control processor 135 includes a joint control system for each joint being actuated and controlled by the endoscope manipulator 231 and bend actuators 232. The output of the inverse kinematics processor 134 is provided to the joint control processor 135 which controls operation of the actuating unit 140 through actuating commands 137 so that controllable joints of the endoscope manipulator 231 and controllably bendable segments of the robotic endoscope 110 are driven to proper positions so as to effect the commanded state of the distal tip 112 of the robotic endoscope 110.

Figure 7:
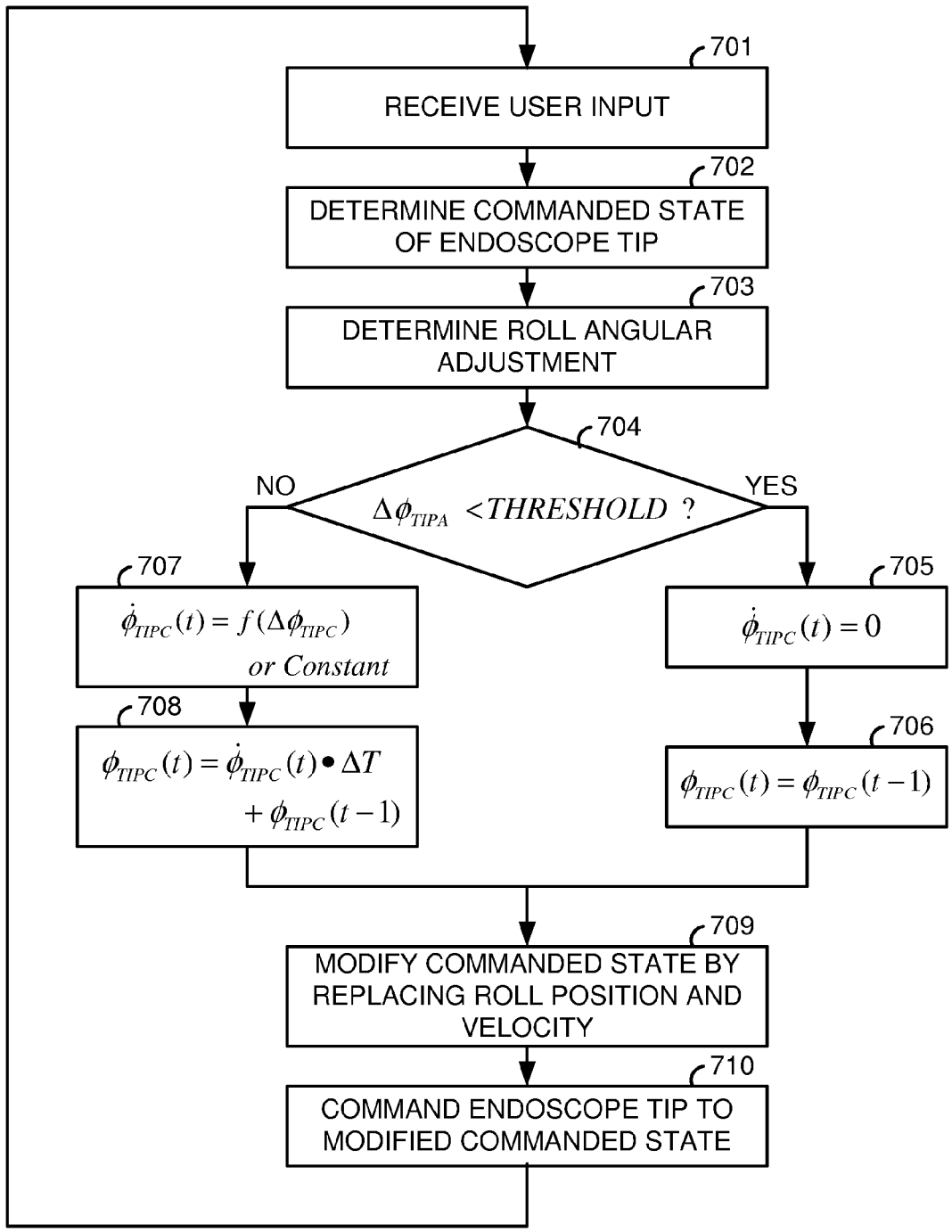
FIG. 7 illustrates a flow diagram of a computer implemented method for controlling operator commanded movement of a distal tip of a robotic endoscope while maintaining a roll orientation at the tip, utilizing aspects of the present invention.

FIG. 7 illustrates, as an example, a flow diagram of a method performed in the input handler processor 131 for controlling operator commanded movement of the distal tip 112 of the robotic endoscope 110 while maintaining a roll orientation at the tip 112 corresponding to the setpoint. In 701, the method receives an operator input from the input control device 171. In 702, the method transforms the operator input to a current commanded state of the distal tip 112 of the endoscope 110 in a conventional manner by applying, for example, the 6 DOF translational and orientational positions and velocities received from the input control device 171 to known transforms to generate the current commanded state in corresponding 6 DOF translational and orientational positions and velocities of the tip 112. The term "current command" as used herein refers to a command issued for the current process cycle or period (e.g., time "t") and the term "prior process command" as used herein refers to a command that had been issued in a prior process cycle or period (e.g., time "t–1").

In 703, the method determines a roll angular adjustment ($\Delta\phi_{TIPA}$) using information of an immediately prior process commanded state of the tip 112 and the setpoint. The roll angular adjustment represents a change in roll angle about the $Z_{TIP}$ axis that is required to maintain the horizontal $X_{TIP}$ axis of the view captured by a camera at the distal tip 112 with the roll orientation indicated by the setpoint. As previously explained in reference to FIG. 5, the setpoint may be operator selected or it may be automatically established using, for example, a gravity sensing mechanism, such as described in previously incorporated by reference U.S. Pat. No. 7,134, 992, in which case, the roll orientation is preferably a horizontal line perpendicular to the downward pointing gravity vector.

Figure 8:
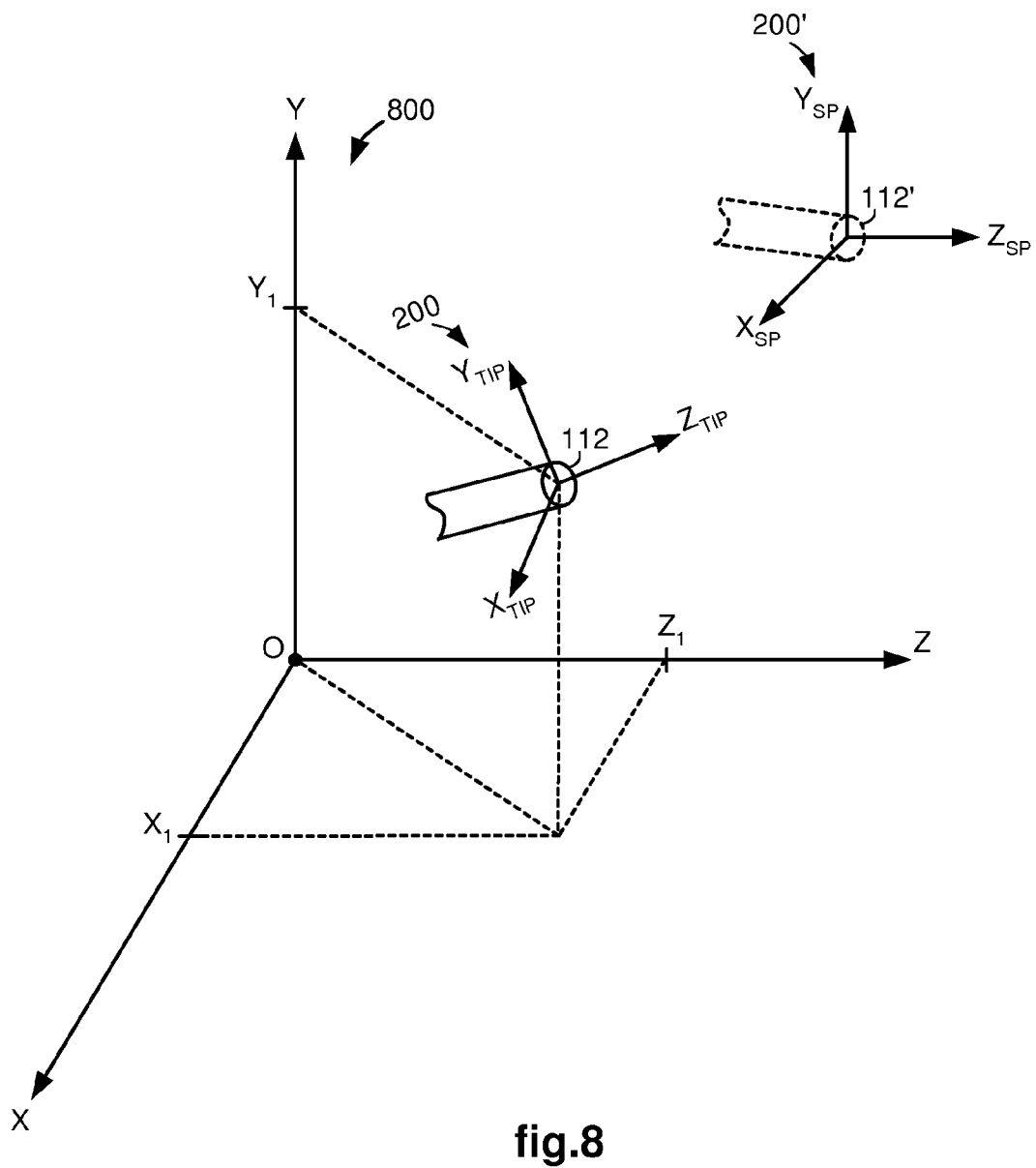
FIG. 8 illustrates a fixed reference frame and a reference frame associated with the distal tip of the robotic endoscope that moves within the fixed reference frame as used in the medical robotic system utilizing aspects of the present invention.
Figure 9:
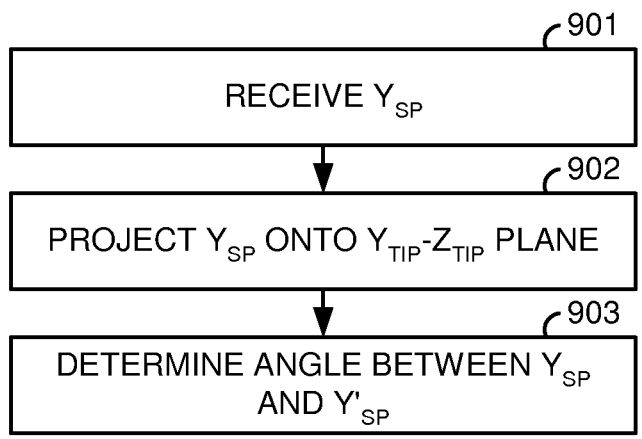
FIG. 9 illustrates a flow diagram of a computer implemented method for determining a roll angular adjustment in the medical robotic system utilizing aspects of the present invention.
Figure 10:
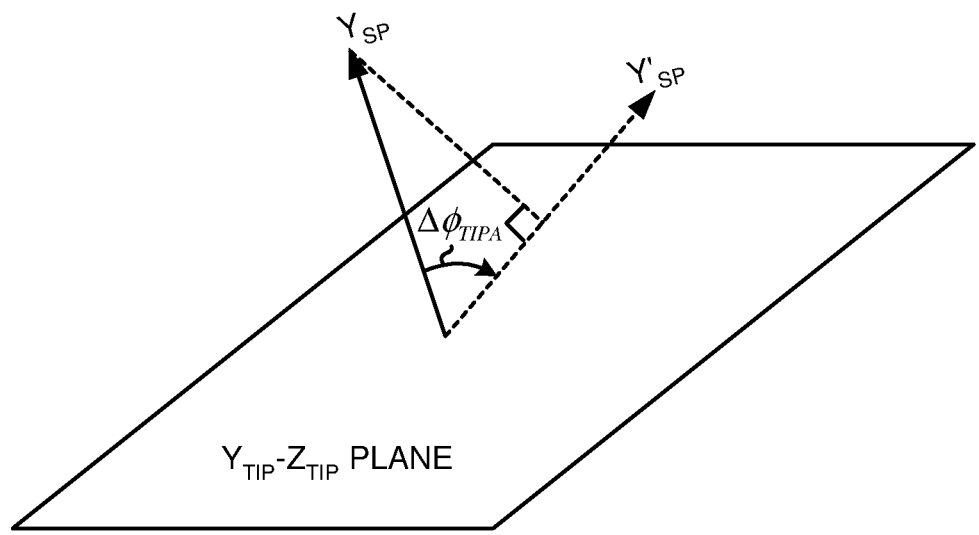
FIG. 10 illustrates a graphical depiction of determining a roll angular adjustment as used in the medical robotic system utilizing aspects of the present invention.

An example of a method for performing 703 is illustrated in FIG. 9, wherein in 901, the reference vector $Y_{SP}$ which is indicative of the setpoint and whose generation was previously described in reference to FIG. 5, is received from the setpoint processor 132. As the distal tip 112 moves and orients in various directions, its distal tip reference frame 200, which has orthogonal axes $X_{TIP}$, $Y_{TIP}$ and $Z_{TIP}$ as defined in reference to FIG. 2, moves accordingly. For example, as shown in FIG. 8, a reference vector $Y_{SP}$ is shown as being established by the operator when the tip 112 was previously at a tip reference frame position and orientation indicated as 200' in a fixed reference frame 800. Subsequent movement of the tip 112 resulted in the tip reference frame position and orientation moving as indicated by tip reference frame 200 in the fixed reference frame 800. In 902, the reference vector $Y_{SP}$ is then projected onto a plane including the $Y_{TIP}$ axis and the $Z_{TIP}$ axis of the tip reference frame, such as shown in FIG. 10. The tip reference frame 200 may be provided in this case from a prior process cycle commanded state of the tip 112 (such as the immediately prior process period as shown in FIG. 5) or it may be provided from information received from the forward kinematics processor 136 that indicates a sensed state of the tip 112. In 903, the roll angle adjustment ($\Delta\phi_{TIPA}$) is then determined as the angle between the reference vector $Y_{SP}$ and its projection $Y'_{SP}$ on the $Y_{TIP}$-$Z_{TIP}$ plane, as also shown in FIG. 10.

In 704, a determination is made whether the roll angular adjustment determined in 703 is less than a threshold value. If the roll angular adjustment is less than the threshold value (i.e., the roll angular adjustment is relatively small), then the method proceeds to 705, otherwise, it proceeds to 707. The threshold value may be set to some fixed value such as 5 degrees or some other angle that results in a change in the roll orientation of the distal camera view as seen in the captured image 350 on the display screen 160 that an operator would find imperceptible or at least would not be disorienting to the operator. To satisfy operator preferences, the GUI described in reference to FIG. 6 may also be modified by adding some means that allows the operator to specify and/or adjust the threshold value.

In 705, since the roll angular adjustment has been determined to be less than the threshold value, then the method modifies the current commanded roll velocity ($\dot{\phi}_{TIPC}$) to zero and in 706, it modifies, if necessary, the current commanded roll position, i.e., $\phi_{TIPC}$ (t), to its immediately prior process cycle commanded roll position, i.e., $\phi_{TIPC}$ (t–1), so that the current roll orientation at the distal tip 112 would be maintained.

On the other hand, in 707, when the roll angular adjustment has been determined to be equal to or more than the threshold value, then the method modifies the current commanded roll angular velocity ($\dot{\phi}_{TIPC}$) to a value that is either a function of the roll angular adjustment or to a constant value, depending upon the selected embodiment of the present invention, and in 708, it modifies the current commanded roll position, i.e., $\phi_{TIPC}$ (t), so as to be consistent with the modified current commanded roll velocity ($\dot{\phi}_{TIPC}$), using for example, the following equation:

$$\phi_{TIPC}(t) = \dot{\phi}_{TIPC}(t) \cdot \Delta T + \phi_{TIPC}(t-1) \tag{1}$$

where "$\phi_{TIPC}(t)$" is the modified current commanded roll velocity, "$\Delta T$" is the duration of the process cycle or period, and "$\phi_{TIPC}(t-1)$" is an immediately prior process period commanded roll position (previously stored in and currently read from storage element or memory 133 in FIG. 5).

Either or both the function and the constant used in 707 may possibly be scaled proportionally with the magnitude of the total commanded tip velocity in order to avoid large and/or abrupt changes that may surprise the operator. In one example of such a function, the function may be constructed so that the current commanded roll velocity ($\phi_{TIPC}$) gets larger as the roll angular adjustment gets larger (with some maximum value). When the current commanded roll velocity ($\phi_{TIPC}$) is set to a constant, such a limiting of the magnitude of the current commanded roll velocity may lengthen the amount of time required to arrive at the current commanded roll position, but will prevent large, potentially dangerous tip velocity commands from occurring.

In 709, the method transforms the operator input to a modified current commanded state of the endoscope tip 112 in a conventional manner such as in 702, except this time the modified current commanded roll velocity is constrained to be equal to the value determined in either 705 or 707 and the modified current commanded roll position is constrained to be equal to the value determined in either 706 or 708, depending upon the result of 704. Alternatively, the modified current command state of the endoscope tip 112 may be simply formed by merely replacing the current commanded roll position in the current commanded state with the modified current roll position and replacing the current commanded roll velocity in the current commanded state with the modified current commanded roll position. In 710, the modified commanded state of the distal tip 112 is then provided to the inverse kinematics processor 134 as previously described in reference to FIG. 5.

Although the various aspects of the present invention have been described with respect to one or more preferred embodiments, it will be understood that the invention is entitled to full protection within the full scope of the appended claims.

What is claimed is:

1. A medical system comprising:
a robotic endoscope having an elongate body including one or more bendable segments and a distal tip;
a manipulator having one or more drivable joints for manipulating the robotic endoscope in corresponding degrees of freedom movement;
an input control device; and
a processor programmed to: receive a control input from the input control device; determine a current commanded state of the tip of the robotic endoscope from the control input wherein the current commanded state includes a commanded roll position and roll velocity; determine a roll angular adjustment by using a difference between a setpoint and the current commanded state of the tip of the robotic endoscope, wherein the setpoint indicates a desired roll orientation of a camera view captured at the tip of the robotic endoscope; determine a modified current commanded roll position by modifying the current commanded roll position to be conditionally related by the roll angular adjustment to a prior process period commanded roll position, and determine a modified current commanded roll velocity by modifying the current commanded roll velocity to be conditionally related by the roll angular adjustment to one of a constant and a function of the roll angular adjustment; modify the current commanded state by constraining the current commanded roll position and roll velocity to be the modified current commanded roll position and roll velocity; and command the tip of the robotic endoscope to be driven to the modified current commanded state.

2. The medical system according to claim 1, wherein a tip reference frame is defined at the tip of the endoscope so as to have a $Z_{TIP}$ axis indicative of a depth direction of a view captured at the tip, a $X_{TIP}$ axis indicative of a horizontal direction of the view, and a $Y_{TIP}$ axis indicative a vertical direction of the view; and wherein the processor is programmed to determine the roll angular adjustment by: receiving a reference vector indicative of the setpoint, projecting the reference vector onto a plane containing the $Y_{TIP}$ axis and the $Z_{TIP}$ axis, and determining the roll angular adjustment as an angle between the reference vector and the projected reference vector.

3. The medical system according to claim 1, where the processor is programmed to modify the current commanded roll velocity by setting it to zero and modify the current commanded roll position by setting it to the prior process period commanded roll position if the roll angular adjustment is less than a threshold value.

4. The medical system according to claim 1, wherein the processor is programmed to modify the current commanded roll velocity by setting the current commanded roll velocity to a fixed value and by modifying the current commanded roll position by setting the current commanded roll position to a sum of the prior process period commanded roll position and a product of the modified current commanded roll velocity and the process period if the roll angular adjustment is greater than or equal to a threshold value.

5. The medical system according to claim 1, wherein the processor is programmed to modify the current commanded roll velocity so as to be a function of the roll angular adjustment and to modify the commanded roll position by setting the commanded roll position to a sum of the prior process period commanded roll position and a product of the modified current commanded roll velocity and the process period if the roll angular adjustment is greater than or equal to a threshold value.

6. The medical system according to claim 1, wherein the setpoint has been established so as to indicate a vector that is orthogonal to gravity.

7. The medical system according to claim 1, wherein the processor is programmed to receive an indication of the setpoint from a setpoint input device.

8. The medical system according to claim 7, wherein the processor is programmed to establish the setpoint so as to indicate a vector that indicates a roll orientation at the tip at the time that the indication of the setpoint is received from the setpoint input device.

9. The medical system according to claim 7, further comprising:
a display screen; and
an orientation adjustment input device;
wherein the processor is programmed to display a graphical representation of the roll setpoint on the display screen, receive an input from the orientation adjustment input device, adjust an orientation of the graphical representation of the roll setpoint on the display screen according to the input received from the orientation adjustment input device, and determine the roll setpoint from the adjusted orientation of the graphical representation of the roll setpoint.

10. The medical system according to claim 1, wherein the processor is programmed to command the tip of the robotic endoscope to be driven to the modified current commanded state by determining a combination of states for the one or more joints of the manipulator and bending angles for the one or more bendable segments of the elongate body so as to achieve the modified current commanded state of the tip of the robotic endoscope; and commanding the one or more joints of the manipulator to be driven to the determined joint states and the one or more bendable segments of the robotic endoscope to be driven to the determined bending angles.

11. The medical system according to claim 10, wherein the one or more joints of the manipulator includes a prismatic joint for moving a proximal end of the robotic endoscope forward and backward along a linear path and a rotary joint for rotating the proximal end of the robotic endoscope about the linear path.

12. The medical system according to claim 6, wherein the processor is programmed to determine the current commanded state of the tip of the robotic endoscope from the control input by determining translational and angular tip states from the control input and stored information of control inputs for one or more prior process periods.

13. The medical system according to claim 10, wherein the processor is programmed to determine the commanded state of the tip of the robotic endoscope from the control input by transforming the control input to a desired state of the tip of the robotic endoscope relative to a fixed Cartesian reference frame.

14. The medical system according to claim 13, wherein the processor is programmed to determine the states of the one or more joints of the manipulator and the bending angles for the one or more bendable segments of the robotic endoscope by applying the modified current commanded state to inverse kinematics of the combined serial kinematic chain composed of the manipulator and the robotic endoscope.

* * * * *